US008048923B2

(12) United States Patent
Brusilow

(10) Patent No.: US 8,048,923 B2
(45) Date of Patent: Nov. 1, 2011

(54) TREATMENT OF POLYGLUTAMINE DISORDERS CAUSED BY EXPANDING GENOMIC CAG NUCLEOTIDES

(75) Inventor: William S. Brusilow, Grosse Pointe, MI (US)

(73) Assignee: Odessa Pharma, Chevy Chase, MD (US)

( * ) Notice: Subject to any disclaimer, the term of this patent is extended or adjusted under 35 U.S.C. 154(b) by 2224 days.

(21) Appl. No.: 10/758,415

(22) Filed: Jan. 16, 2004

(65) Prior Publication Data

US 2004/0152778 A1 Aug. 5, 2004

Related U.S. Application Data

(60) Provisional application No. 60/440,627, filed on Jan. 17, 2003.

(51) Int. Cl.
*A61K 31/198* (2006.01)
(52) U.S. Cl. ........................................ 514/561; 514/562
(58) Field of Classification Search .................. 514/561, 514/562
See application file for complete search history.

(56) References Cited

U.S. PATENT DOCUMENTS

2002/0173537 A1* 11/2002 Feuerstein et al. .......... 514/424

OTHER PUBLICATIONS

Hertz et al., "Astrocytes:Glutamate Producers for Neurons", Journal of Neuroscience Research, 57:417-428 (1999).
Apostol et al., "A cell-based assay for aggregation inhibitors as therapeutics of polyglutamine-repeat disease and validation in *Drosophila*", Proceedings of the National Academy of Sciences May 13, 2003 100 (10):5950-5955.
Swanson et al., "Methionine Sulfoximine Reduces Cortical Infarct Size in Rats After Middle Cerebral Artery Occlusion", Stroke, vol. 21, No. 2, Feb. 1990, pp. 322-327.
Lamar et al., "The duration of the inhibition of glutamine synthetase by methionine sulfoximine", Biochemical Pharmacology, vol. 17, pp. 636-640, 1968.
Takahashi et al., "Inhibition of brain glutamine accumulation prevents cerebral edema in hyperammonemic rats", The American Physiological Society, 1991, pp. H825-H829.
Hack et al., "Glufosinate Ammonium-Some aspects of its mode of action in mammals", FD CHEM.Toxic., vol. 32; No. 5, pp. 461-470, 1994.
Gill et al., "The crystal structure of phosphinothricin in the active site of glutamine synthetase Illuminates the Mechanism of Enzymatic Inhibition", Biochemistry 2001, 40, 1903-1912.
Blei, Andres T., et al., "Ammonia-Induced Brain Edema and Intracranial Hypertension in Rats After Portacaval Anastomosis," *Hepatology* 19(6):,1437-1444, Jun. 1994.
Brusilow, Saul W. "Inborn Errors of Urea Synthesis," *In: Scriver CR, Lloyd Jk, eds. Genetic and Metabolic Disease in Pediatrics*. 5: 140-165, London: Butterworths, 1985.

Brusilow, Saul W., et al., "Urea Cycle Disorders: Diagnosis, Pathophysiology, and Therapy," *Advances in Pediatrics* 43:127-170, 1996.
Butterworth, R.F., "Effects of Hyperammonaemia on Brain Function," *J. Inher. Metab. Dis.* 21(1):6-20, 1998.
Cordoba, Juan, et al., "Brain Edema and Hepatic Encephalopathy," *Seminars in Liver Disease* 16(3): 271-280, 1996.
Folbergrova, J., "Free Glutamine Level in the Rat Brain in Vivo After Methionine Sulphoximine Administration," *Physiologia Bohemoslovenica* 13:21-26, 1963.
Gershoff, S.N., et al.,"The Relative Effect of Methionine Sulfoximine on Different Animal Species," *J. Nutr.* 45:451-458, 1951.
Häussinger, Dieter, et al.,"Pathogenesis of Hepatic Encephalopathy," *Journal of Gastroenterology and Hepatology* 17:5256-S259, 2002.
Hawkins, Richard, et al., "Effect of Reducing Brain Glutamine Synthesis on Metabolic Symptoms of Hepatic Encephalopathy," *Journal of Neurochemistry* 60(3):1000-1006, 1993.
Hawkins, Richard, et al., "Hyperammonaemia Does Not Impair Brain Function in the Absence of Net Glutamine Synthesis," *Biochem. J.* 277:697-703, 1991.
Hirata, Takahiko, et al., "Impaired Pial Arteriolar Reactivity to Hypercapnia During Hyperammonemia Depends on Glutamine Synthesis," *Stroke* 27(4): 729-736, 1996.
Jonung, Torbjorn, et al., "Methionine Sulfoximine Prevents the Accumulation of Large Neutral Amino Acids in Brain of Hyperammonemic Rats," *J. Surgical Research* 36:349-353, 1984.
Krakoff, Irwin H., et al., "Effect of Methionine Sulfoximine in Man," *J. Pharm. Experimenetal Ther.* 2:599-604, 1961.
Lamar, C., et al., "The Duration of the Inhibition of Glutamine Synthetase by Methionine Sulfoximine," *Biochemical Pharmacology* 17:636-642, 1968.
Master, Sonali, et al., "Cerebral Blood Flow and the Development of Ammonia-Induced Brain Edema in Rats After Portacaval Anastomosis," *Hepatology* 30(4): 876-880, 1999.
Norenberg, Michael D., et al,"Fine Structural Localization of Glutamine Synthetase in Astrocytes of Rat Brain," *Brain Research* 161:303-310, 1979.
Richman, Paul G., et al., "Inhibition of γ-Glutamylcystein Synthetase by L-Methionine-S-Sulfoximine," *J. Biological Chemistry* 248(19): 6684-6690, 1973.
Rowe, W. Bruce, et al., "Identification of L-Methionine-S-Sulfoximine as the Convulsant Isomer of Methionine Sulfoximine," *Proceedings of the National Academy of Sciences* 66(2): 500-506, Jun. 1970.
Sellinger, Otto Z., et al., "Methionine Sulfoximine Seizures. VII. the Dissociation of the Convulsant and Glutamine Synthetase Inhibitory Effects," *J. Pharmacology & Experimental Therapeutics* 161(1): 212-222, 1968.

(Continued)

*Primary Examiner* — Jeffrey S. Lundgren
*Assistant Examiner* — Zohreh Vakili
(74) *Attorney, Agent, or Firm* — Rothwell, Figg, Ernst & Manbeck, P.C.

(57) ABSTRACT

The present invention relates to the treatment or prevention of neurodegenerative polyglutamine diseases by the administration of effective amounts of L-methionine S-sulfoximine, L-ethionine S-sulfoximine, glufosinate and/or branched chain α-keto acids. In particular, the present invention relates to the treatment or prevention of Huntington's disease and other polyglutamine disorders caused by expanded genomic CAG nucleotides.

9 Claims, No Drawings

OTHER PUBLICATIONS

Sugimoto, Hideyoshi, et al., "Methionine Sulfoximine, a Glutamine Synthetase Inhibitor, Attenuates Increased Extracellular Potassium Activity During Acute Hyperammonemia," *Journal of Cerebral Blood Flow & Metabolism*, 17:44-49, 1997.

Takahashi, Hideo, et al., "Inhibition of Brain Glutamine Accumulation Prevents Cerebral Edema in Hyperammonemic Rats," *American Physiological Society* 261:H825-H829, 1991.

Voorhies, Theresa M., "Acute Hyperammonemia in the Young Primate: Physiologic and Neuropathologic Correlates," *Pediatric Research* 17(12):970-975, 1983.

Wada, Juhn A., et al., "The Susceptibilty of Auditory Stimuli of Animals Treated with Methionine Sulfoximine," *Experimental Neurology* 15:157-165, 196.

Warren, Kenneth S., et al., "Effect of an Inhibitor of Glutamine Synthesis (Methionine Sulfoximine) on Ammonia Toxicity and Metabolism," *J. Lab. & Clin. Med.* 64(3): 442-449, 1964.

Watson, Alan J., et al. "Transient Idiopathic Hyperammonaemia in Adults," *The Lancet* 1271-1274, Dec. 7, 1985.

Willard-Mack, C.L., et al., "Inhibition of Glutamine Synthetase Reduces Ammonia-Induced Astrocyte Swelling in Rat," *Neuroscience* 71(2): 589-599, 1996.

Zwingmann, Claudia, et al., Multinuclear NMR Spectroscopy Studies on NH4CI-Induced 7Metabolic Alterations and Detoxification Processes in Primary Astrocytes and Glioma Cells, *Dev. Neurosci* 20:417-426, 1998.

Apostolakis et al., Brain Research Bulletin, vol. 23, pp. 257-262 (1989).

Ginefri-Gayet et al., Pharmacology Biochemistry and Behavior, vol. 43, pp. 173-179 (1992).

Takahashi et al., Circulation Research, 71(5), 1220-1230 (Nov. 1992).

Harth et al., J. Exp. Med., 189(9), 1425-1435 (May 3, 1999).

* cited by examiner

TREATMENT OF POLYGLUTAMINE DISORDERS CAUSED BY EXPANDING GENOMIC CAG NUCLEOTIDES

CROSS REFERENCE TO RELATED APPLICATION

This application claims the benefit of U.S. Provisional Application No. 60/440,627, filed Jan. 17, 2003.

BACKGROUND OF THE INVENTION

1. Field of the Invention

The present invention relates, generally, to the treatment or prevention of neurodegenerative polyglutamine by the administration of effective amounts of L-methionine S-sulfoximine, L-ethionine S-sulfoximine, glufosinate and/or branched chain α-keto acids. In particular, the present invention relates to the treatment of Huntington's disease and other polyglutamine disorders caused by expanded genomic CAG nucleotides.

2. Description of Related Art

There are a number of neurodegenerative polyglutamine diseases, for example Huntington's disease, spinocerebellar ataxia, and spinobulbar muscular atrophy (Kennedy's Disease), which are characterized by expanded genomic CAG sequences resulting in the synthesis and accumulation of polyglutamine tracts in brain proteins of unknown function (e.g. Huntingtin in Huntington's disease and ataxin in spinocerebellar ataxias) that are responsible for the neurologic problem. The CAG codon is translated into glutamine (Q). Proteins with expanded polyglutamine domains aggregate and aggregation is a pathologic hallmark of the polyglutamine repeat diseases (Hackam, A. S. et al. J Cell Biol 141, 1097-1105 (1998); Perez, M. K. et al. J Cell Biol 143, 1457-1470 (1998)). These polyglutamine length-dependent properties may arise from the ability of long polyglutamine domains to adopt unique three-dimensional conformations and serve to confer the disease proteins with a pathologic gain-of-function (Perutz, M. F. Trends Biochem Sci 24, 58-63 (1999); Lansbury, P. T. J. Proc Natl Acad Sci USA 96, 3342-3344 (1999)).

All diseases in the CAG repeat family show genetic anticipation, meaning the disease usually appears at an earlier age and increases in severity with each generation. Genetic anticipation is linked to increasing numbers of CAG repeats, which result from expansion of the unstable CAG sequence when reproductive cells divide to form eggs and sperm. In general, neurodegenerative disorders are progressive (i.e., their symptoms are not apparent until months or more commonly years after the disease has begun), and caused by an initial reduction of neuronal function, followed by a complete loss of function upon neuronal death.

Huntington's Disease (HD) is a devastating, degenerative brain disorder for which there is, at present, no effective treatment or cure. HD slowly diminishes the affected individual's ability to walk, think, talk and reason. Eventually, the person with HD becomes totally dependent upon others for his or her care. Huntington's Disease profoundly affects the lives of entire families: emotionally, socially and economically. Early symptoms of Huntington's Disease may affect cognitive ability or mobility and include depression, mood swings, forgetfulness, clumsiness, involuntary twitching and lack of coordination. As the disease progresses, concentration and short-term memory diminish and involuntary movements of the head, trunk and limbs increase. Walking, speaking and swallowing abilities deteriorate. Eventually the person is unable to care for him or herself. Death follows from complications such as choking, infection or heart failure. HD typically begins in mid-life, between the ages of 30 and 45, though onset may occur as early as the age of 2. Children who develop the juvenile form of the disease rarely live to adulthood. HD affects males and females equally and crosses all ethnic and racial boundaries. Each child of a person with HD has a 50/50 chance of inheriting the fatal gene. HD is an autosomal dominant condition and thus everyone who carries the gene will develop the disease.

The Huntington's Disease (HD) gene was mapped to chromosome 4p16.3 in 1983 but eluded identification until 1993. When finally identified, the gene (IT15) was found to contain a CAG repeat within its 5'-end coding sequence (Cell 72:971-983). This CAG repeat is expanded in individuals with HD who may or may not be symptomatic. However, the presence of a CAG repeat expansion is found in virtually all symptomatic HD individuals (N. Engl. J. Med. 330:1401-1406).

Normal HD gene CAG repeats range from 10-29 repeats. Some normal individuals (<1%) have been found with intermediate HD gene CAG repeats of 30-35 repeats. Individuals affected with HD typically have at least one HD gene CAG repeat of 36 repeats or greater. It was also found that in a few rare instances (10 cases) individuals having repeats of 36-39 repeats had remained asymptomatic by standard clinical criteria at advanced age. In one exceptional case, a 95 year old patient had 39 repeats (Rubinsztein et. al., 1996; Am. J. Hum. Genet. 59:16-22). There is a tendency to an earlier age-of-onset of HD symptoms with increasing CAG repeat number. A review of 1,049 people (the majority of whom were symptomatic) has provided a determination of the likelihood of an age-of-onset for a given CAG repeat size for repeats between 39-50 repeats (Brinkman et al., 1997; Am. J. Hum. Genet. 60:1202-1210). The polyglutamine expansion results in the formation of insoluble, high molecular weight protein aggregates similar to those seen in Alzheimer's disease (Scherzinger et al., Cell 90:549-558 [1997]). Postmortem examination of the brains of patients suffering from Huntington's disease revealed that CAG repeat length positively correlates with the degree of DNA fragmentation within the afflicted striatum (Butterworth et al., Neurosci., 87:49-53 [1998]), indicating that neuronal degeneration observed in Huntington's disease may also occur through an apoptotic process.

Spinocerebellar ataxias are a group of autosomal dominantly inherited ataxias with heterogeneous presentation. Characteristic CAG repeat expansions in the coding sequences at several loci have been detected for certain of these disorders.

Kennedy disease is caused by a specific mutation (an expansion of the normally polymorphic CAG trinucleotide repeat) in the first exon of the androgen receptor gene (which encodes polyglutamine tracts) which is located on the X-chromosone. Similar to Huntington's disease, in this disease CAG is also abnormally repeated. The CAG repeat range in the general population is approximately 12 to 32 repeats. In patients with Kennedy disease, the repeats may number as many as 40 to 55 repeats. Symptoms appear when the repeats exceed about 40. A larger number of repeats has been suggested to cause symptoms to begin earlier in life and progress more rapidly.

Currently, physicians may prescribe a number of medications to help control emotional and movement problems associated with polyglutamine disorders caused by expanded genomic CAG nucleotides. Such medications include antipsychotic drugs, such as haloperidol, or other drugs, such as clonazepam, to alleviate choreic movements and also to help control hallucinations, delusions, and violent outbursts; fluoxetine, sertraline, nortriptyline, or other compounds may be prescribed for depression. Tranquilizers can help control anxiety and lithium may be prescribed to combat pathological excitement and severe mood swings. It is important to remember however, that while medicines may help keep these clinical symptoms under control, there is currently no treatment to stop or reverse the course of the disease.

Several models have been developed for the polyglutamine-repeat diseases to model different aspects of disease including mouse, rat, *Caenorhabditis elegans, Drosophila*, yeast and numerous cell-culture systems (Neuron 35, 819-822; Trends Genet. 18, 202-209; Proc Natl Acad Sci USA. 2003 May 13; 100 (10): 5950-5955).

Remacemide and Coenzyme Q10 have been tested for the treatment of HD but a large-scale clinical trial that tested the ability of these investigational drugs to slow the progression of Huntington's disease showed that neither drug resulted in any significant improvement for the patients. Remacemide blocks a neurotransmitter in the brain (the NMDA glutamate receptor) which has long been suspected of contributing to the death of brain cells in Huntington's disease. Coenzyme Q10 is a substance that occurs naturally in the body and plays a role in the function of mitochondria, the energy factories of human cells. It is also an anti-oxidant, meaning that it can neutralize potentially injurious oxygen-containing chemicals called free radicals, which may play a role in the nerve cell death that occurs in Huntington's disease. After one year of treatment, the disease seemed to progress more slowly in patients treated with Coenzyme Q10, however, the investigators concluded that overall the results were inconclusive as to whether there is real benefit from this drug (*Neurology*, Aug. 14, 2001; 57: 397).

An experimental drug called cystamine has been found to alleviate tremors and prolong life in mice with the gene mutation for Huntington's disease (HD). The drug appears to work by increasing the activity of proteins that protect nerve cells, or neurons, from degeneration. The brains of Huntington's patients become clogged with clumps of protein called aggregates. The aggregates are made up of the abnormal huntingtin proteins hooked together. The aggregations are formed by the action of an enzyme called transglutaminase and by the tendency of these proteins to stick together. Cystamine inactivates an enzyme called transglutaminase and thus would theoretically prevent clumps of huntingtin protein (Nature Medicine 8, 143-149, 2002). Surprisingly, cystamine was found to increase the levels of certain neuroprotective proteins.

As discussed above, currently used treatments are primarily directed at symptomatic relief and provide poor long term disease management. Thus, new methods for the treatment of neurodegenerative diseases, including but not limited to Huntington's disease, spinocerebellar ataxia, and spinobulbar muscular atrophy (Kennedy's Disease) that are effective and convenient, but lack significant side effects are needed.

SUMMARY OF THE INVENTION

The primary object of the present invention is to provide a treatment for polyglutamine disorders caused by expanded genomic CAG nucleotides by reducing the availability of free glutamine in astrocytes, the source of glutamine for neurons and thereby preventing or reducing the biosynthesis of toxic proteins in this group of diseases and others by treatment with pharmacologic agents used either singly or in combination.

The present invention achieves the above discussed objective by the administration of effective amounts of L-methionine S-sulfoximine, L-ethionine S-sulfoximine, glufosinate and/or branched chain α-keto acids.

Further features and advantages of the present invention, are described in detail below.

DETAILED DESCRIPTION OF THE INVENTION

The blood brain barrier excludes many amino acids from neurons, and thus specific physiologic methods have evolved to provide amino acids for neurons. Glutamine is supplied to neurons by astrocytes via the glutamine-glutamate cycle. The mechanism works as follows: Glutamine is synthesized from ammonia and glutamate catalyzed by glutamine synthetase in astrocytes, which are the only cells in the brain rich in glutamine synthetase. The glutamine so produced is transported to neurons where it is used for protein synthesis (e.g. huntingtin) and deamidated to produce glutamate which serves many functions. Because the accumulation of glutamate is toxic, it is transported back to the astrocytes and resynthesized to glutamine to repeat the cycle.

L-methionine S-sulfoximine (MSO) is an irreversible inhibitor (Biochem Pharma 1968:17; 636-640) of glutamine synthetase, an astrocyte specific enzyme (Science 1977:195: 1356-1358) that catalyzes the biosynthesis of glutamine from ammonia and glutamate. MSO, when administered to normal animals, reduces brain levels of glutamine from 5.6 to 1.8 (mmol/kg brain) (AM J. physiol 1991: 261; H825-829). The administration of MSO to a patient suffering from a polyglutamine disorder caused by expanded genomic CAG nucleotides will result in a reduction in the intracellular pool of glutamine and glutaminyl-tRNA and impair the synthesis and accumulation of the toxic polyglutamine protein thereby preventing, ameliorating or delaying neurologic damage. MSO can be administered at a dose of about 2.0-10.0 mg/kg per 6-10 days and is preferably administered orally or intravenously. If the MSO is administered intrathecally the dosage should be about 1.0-5.0 mg/kg per 6-10 days.

Glufosinate (FD Chem Toxic 1994:32; 461-470), ammonium-D-L-homoalanine-4-yl(methyl)-phosphinate, is also a catalytic inhibitor of glutamine synthetase which must be administered intrathecally at a dose of 1.0-5.0 mg per 6-10 days because it does not cross the blood brain barrier. However, when administered in that manner, it operates by the same mechanism as does MSO (Biochemistry 2001:440; 1903-1912).

The α-keto derivatives of the three branched-chain amino acids leucine, valine and isoleucine can substitute for these three essential amino acids in the diet. They cross the blood brain barrier where they are transaminated by glutamate to form the cognate amino acid and α-keto glutarate, thereby reducing brain glutamate levels. The resultant amino acids can be used for protein synthesis or can cross the blood brain barrier and be transported throughout the body, where they will subsequently be used for protein synthesis or metabolized to other compounds. Since brain glutamine and glutamate do not cross the blood brain barrier in appreciable amounts, the net result is a reduction of brain glutamate, thereby reducing the amount of glutamine synthesized by astrocytes. The salts of α-keto-isocaproate (α-keto leucine), α-keto-β-methylbutyrate (α-keto valine) and α-keto-valerate (α-keto isoleucine) can be administered to reduce the availability of glutamine for the synthesis of polyglutamine proteins thereby preventing, ameliorating or delaying neurologic damage. Branched-chain α-keto acids have been tested for efficacy in the treatment of hyperammonemia and of hepatic encephalopathy but not in the treatment of polyglutamine diseases. The α-keto acids can be administered in a dosage of about 100-500 mg/kg body weight, preferably 280-380 mg/kg body weight.

One or more compounds according to the present invention can be formulated into compositions along with other compounds known to be useful for the treatment of polyglutamine diseases. Such compounds include but are not limited to neuroprotective compounds and compounds which inhibit aggregate formation or inhibit transglutaminase. Examples of such compounds include but are not limited to minocycline, ethyl eicosapeninoate, riluzole, Congo red, cysteamine and cystamine. The compounds according to the present invention can also be included in kits which comprise L-methionine S-sulfoximine, L-ethionine S-sulfoximine, glufosinate and/or branched chain α-keto acids in separate containers along with other compounds known to be useful for the treatment of polyglutamine diseases in separate containers. The compounds can be mixed to produce custom formulated compositions or the compounds can be administered separately.

The compounds can be administered prior to the appearance of symptoms in order to delay or prevent the occurrence of symptoms.

The formulations of the present invention include those suitable for oral, rectal, nasal, inhalation (e.g., to the lungs), buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations suitable for oral administration may be controlled release or osmotic dosage forms.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for nasal, parenteral, or inhalation administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents.

The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound, in a unit dosage form in a sealed container. The compound or salt is provided in the form of a lyophilizate which is capable of being reconstituted with a suitable pharmaceutically acceptable carrier to form a liquid composition suitable for injection thereof into a subject. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis/tris buffer (pH 6) or ethanol/water and contain from 0.1 to 0.2M active ingredient.

Further, the present invention provides liposomal formulations of the active compounds disclosed herein. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

The liposomal formulations containing the compounds disclosed herein, may be lyophilized to produce a lyophilizate which may be reconstituted with a pharmaceutically acceptable carrier, such as water, to regenerate a liposomal suspension.

Other pharmaceutical compositions may be prepared from the compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The therapeutically effective dosage or treatment effective amount of any one active agent will vary somewhat from compound to compound as discussed above, and patient to patient (depending upon the age and condition of the subject), and will depend upon factors such as the age and condition of the patient and the route of delivery. Such dosages can be determined in accordance with routine pharmacological procedures known to those skilled in the art. The compounds can be administered prior to the appearance of symptoms in order to delay or prevent the occurrence of symptoms.

Administration may be carried out on a chronic or acute basis. When the administering step is an acute administering step, the active agent may (for example) be given as a single dosage as above, or daily in the above dosages for a period of 6-10 days. Where the administering step is a chronic administrating step, the daily dosage will be given at least 3, 4 or 5 times a week (e.g., seven days a week) for a period of at least two weeks, at least a month, at least two months, or even at least six months or more. When a chronic dosage regimen is completed the patient may be reevaluated and the administration continued or modified as necessary.

As used herein, the term "administering to the brain of a subject" refers to the use of routes of administration, as are known in the art, that provide the therapeutic compound to the central nervous system tissues, and in particular the brain, of a subject being treated.

The blood-brain barrier presents a barrier to the passive diffusion of substances from the bloodstream into various regions of the CNS. However, active transport of certain agents is known to occur in either direction across the blood-brain barrier. Substances that may have limited access to the brain from the bloodstream can be injected directly into the cerebrospinal fluid. Cerebral ischemia and inflammation are also known to modify the blood-brain barrier and result in increased access to substances in the bloodstream.

Administration of a therapeutic compound directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical compound into the cerebrospinal fluid ("spinal injection") is known in the art, and is suited for administration of the present therapeutic compounds.

Pharmacologic-based procedures are also known in the art for circumventing the blood brain barrier, including the conversion of hydrophilic compounds into lipid-soluble drugs. The active agent may be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with therapeutic compounds to be delivered to the interstitial fluid compartment of the brain, to cause an increase in the permeability of the blood-brain barrier and effect increased delivery of the therapeutic compounds to the brain. Intravenous or intraperitoneal administration may also be used to administer the compounds of the present invention.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. Examples of suitable carriers include pyridinium, fatty acids, inositol, cholesterol, and glucose derivatives. The carrier may be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 to Pardridge et al. These chimeric peptides comprise a pharmaceutical agent conjugated with a transportable peptide capable of crossing the blood-brain barrier, by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198 to Poduslo et al. Specific carrier molecules disclosed include hemoglobin, lysozyme, cytochrome c, ceruloplasmin, calmodulin, ubiquitin and substance P. See also U.S. Pat. No. 5,017,566 to Bodor.

Subjects to be treated by the methods of the present invention are typically human subjects, but may also be animal subjects (particularly mammalian subjects) such as dogs, cats, rats, mice, insects, etc., for veterinary purposes, or for drug design and screening purposes. The subjects may be afflicted with a polyglutamine repeat disease, or at risk of developing symptoms associated with a polyglutamine repeat disease, or a subject suspected of being afflicted with a polyglutamine repeat disease.

The following examples are intended to illustrate but not limit the present invention.

EXAMPLE 1

A cell-based assay is used to show that MSO inhibits expanded polyQ protein interactions and/or inclusion formation. Differentiated inducible PC12 cells (Proc Natl Acad Sci USA. 2003 May 13; 100 (10): 5950-5955) are tested for visible aggregate production in the presence and absence of MSO. Cells ($1 \times 10^6$) are plated in 10-cm plates using tissue culture medium low in glutamine to ensure that most of the glutamine in the cells is the product of de novo synthesis by cellular glutamine synthetase. Preliminary growth experiments are conducted to determine the medium formulation with the lowest level of medium glutamine required to supplement de novo synthesis for optimal growth of the cells. MSO is added directly to the cell-culture media at final concentrations of 1-100 μM. The cells are grown overnight and aggregation is calculated. Inhibition of aggregation proceeds in a concentration-dependent manner. Visual counts of aggregates are performed by using fluorescent microscopy. MSO is found to inhibit aggregation.

EXAMPLE 2

*Drosophila* (e.g. the transgenic polyQ line P{UAS-Q48myc}[42]) is used to show that MSO reduces polyglutamine pathogenesis in vivo. Flies are mated at 25° C. as described in Nature 413, 739-743. Eggs are collected and transferred into vials at 29° C. containing standard food supplemented with MSO, and adults are transferred to vials containing fresh food every 3 days after eclosion. Eyes are monitored at 3, 7, and 10 days after eclosion by using the pseudopupil technique (Nature 413, 739-743). The neurodegeneration is observed most easily in the fly compound eye, in which photoreceptor cells produce a repeating trapezoidal arrangement of seven visible rhabdomeres (subcellular light-gathering structures) (Hum. Mol. Genet. 9, 13-25; Science 287, 1837-1840; Neuron 21, 633-642; Proc Natl Acad Sci USA. 2003 May 13; 100 (10): 5950-5955). As a primary assay, the effect of MSO on the integrity of photoreceptor neurons in the compound eye is evaluated. The expression of a polypeptide with 48 glutamines (Q48) leads to a progressive loss of rhabdomeres.

A second phenotype associated with expanded polyQ expression is a decrease in motor function. This is assayed by using an "escape" or climbing assay as described in Exp. Gerontol. 13, 189-196. Flies with polyglutamine-induced neuropathology (Q48) need an average of 26 sec to climb a defined distance up a vial. Similar flies fed MSO require less time to climb the same distance, reflecting significant rescue of motor function.

EXAMPLE 3

In order to show that the inhibition of glutamine by MSO is reducing neuronal toxic protein synthesis, L-glutamine (L-GLN) is added to an MSO treated culture of differentiated inducible PC12 cells (Proc Natl Acad Sci USA. 2003 May 13; 100 (10): 5950-5955) as described in example 1. The addition of L-glutamine reverses the decreased glutamine and glutamate levels due to the inhibitory effect of MSO on the cells and results in increased toxic protein synthesis and aggregation. In contrast, the addition of L-GLN has no effect on the growth of cells not treated with MSO or cultures treated with subinhibitory concentrations of MSO.

I claim:

1. A method for treating a polyglutamine disease, comprising administering a compound selected from the group consisting of L-methionine S-sulfoximine, L-ethionine S-sulfoximine, glufosinate to a patient in need of such treatment.

2. The method according to claim 1, wherein said polyglutamine disease is selected from the group consisting of Huntington's disease, spinocerebellar ataxia, and spinobulbar muscular atrophy.

3. The method according to claim 1, wherein said compound is L-methionine S-sulfoximine or L-ethionine S-sulfoximine administered orally, intravenously, or intrathecally.

4. The method according to claim 1, wherein said L-methionine S-sulfoximine or L-ethionine S-sulfoximine is administered intrathecally at a dosage between 1.0-5.0 mg/kg per 6-10 days.

5. The method according to claim 1, wherein said L-methionine S-sulfoximine or L-ethionine S-sulfoximine is administered orally or intravenously at a dose between 2.0-10.0 mg/kg per 6-10 days.

6. The method according to claim 1, wherein said compound is glufosinate administered intrathecally at a dose of 1.0-5.0 mg per 6-10 days.

7. The method according to claim 1, further comprising administering a second compound which inhibits aggregate formation, inhibits transglutaminase, inhibits caspase, or is neuroprotective.

8. The method according to claim 7, wherein said second compound is selected from the group consisting of Congo red, cystamine, cysteamine, minocycline, ethyl eicosapentaenoate, and riluzole.

9. A method for treating a polyglutamine disease caused by expanded genomic CAG nucleotides, comprising administering L-methionine S-sulfoximine to a patient suffering from a polyglutamine disease is selected from the group consisting of Huntington's disease, spinocerebellar ataxia, and spinobulbar muscular atrophy.

* * * * *